United States Patent [19]
Potts et al.

[11] Patent Number: 5,170,887
[45] Date of Patent: Dec. 15, 1992

[54] CONDOM PACKAGING AND DONNING DEVICE

[75] Inventors: D. Malcolm Potts, London, England; Robert G. Wheeler, Greenbank, Wash.; W. Carl Coleman; Wayne Hoofnagle, both of Seattle, Wash.

[73] Assignee: Family Health International, Research Triangle Park, N.C.

[21] Appl. No.: 744,419

[22] Filed: Aug. 13, 1991

[51] Int. Cl.5 .............................................. B65D 85/08
[52] U.S. Cl. .................................... 206/69; 128/844
[58] Field of Search ................... 206/69; 128/842, 844, 128/918; 604/347

[56] References Cited

U.S. PATENT DOCUMENTS

| | | | |
|---|---|---|---|
| 2,365,556 | 12/1944 | Karg | 206/69 |
| 2,389,831 | 11/1945 | Welsh | 2/21 |
| 2,433,538 | 12/1947 | Warner | 128/294 |
| 3,136,417 | 6/1964 | Clinch | |
| 3,282,414 | 11/1966 | Penksa | 206/69 |
| 3,456,784 | 7/1969 | Sirago | 206/78 |
| 3,677,225 | 7/1972 | Czirely | 206/69 X |
| 3,976,076 | 8/1976 | Beach | 128/295 |
| 4,275,812 | 6/1981 | Poncy | 206/278 |
| 4,475,910 | 10/1984 | Conway | 604/352 |
| 4,484,918 | 11/1984 | Omley | 604/349 |
| 4,834,113 | 5/1989 | Reddy | 128/830 |
| 4,840,187 | 6/1989 | Brazier | 206/69 X |
| 4,867,176 | 9/1989 | Lash | 128/830 |
| 4,875,491 | 10/1989 | Parrone | 128/844 |
| 4,961,734 | 10/1990 | Kassman | 206/69 X |
| 4,972,850 | 11/1990 | Broad | 128/844 |
| 4,987,905 | 1/1991 | Broad, Jr. | 206/69 |
| 5,005,695 | 4/1991 | Tennefos | 206/69 |

FOREIGN PATENT DOCUMENTS

| | | | |
|---|---|---|---|
| 9008522 | 8/1990 | PCT Int'l Appl. | 128/918 |
| 2225721 | 6/1990 | United Kingdom | 128/844 |

Primary Examiner—William I. Price
Attorney, Agent, or Firm—Olive & Olive

[57] ABSTRACT

A condom package and donning device, comprising an enclosure and one or more condom attachment means. When the enclosure is separated into enclosure pieces, the condom opening is exposed for donning. When there are attachment means affixed to more than one enclosure piece, opening the device causes separation of the attachment means from each other, causing the proximal end of the attached condom to open for donning the condom. The condom may be released from the package device after donning.

10 Claims, 3 Drawing Sheets

CONDOM PACKAGING AND DONNING DEVICE

BACKGROUND OF THE INVENTION

1. Related Art

Co-pending, commonly assigned U.S. patent applications Ser. Nos. 07/199,030, filed May 26, 1988, now abandoned, and 07/271,884, filed Nov. 15, 1988, now U.S. Pat. No. 4,964,416 of Robin G. Foldesy and Robert G. Wheeler.

2. Field of the Invention

This invention relates generally to condoms, and more particularly to a device for packaging and donning condoms.

3. Description of the Related Art

The recent significant increase in the incidence and spread of sexually transmitted diseases (STD's) has resulted in increased use of condoms as a prophylactic measure to reduce the risk of infection and transmission of STD's.

Condoms generally comprise elongated thin, flexible, tubular sheaths made of a resilient, rubber-like material, such as rubber or various thermoplastic elastomers. Condoms and other devices, such as urine receptacles that fit over a penis are often difficult for the user to put on due to the small size of the device opening, and the resistance to stretching of the open end of the device, which typically comprises an annular ring designed for a tight fit.

During manufacture, condoms made of rubber or other quite stretchable materials are typically rolled which makes them easier to package, store and apply, than if they were packaged unrolled. Even when condoms are so packaged, donning rolled condoms is difficult because the user must pull the rubbery opening area apart and widen the opening with his fingers to don the condom. Further, many condoms are sold with a lubricant coating thereon, which often makes it difficult to grasp the condom prior to and during the donning of the condom.

The structures of the open end of condoms and similarly shaped surgical devices have been varied, for example, by widening the opening, to attempt to make it easier to don condoms, while still providing devices that do not inadvertently slip out of place.

The patent of Hessel (U.S. Pat. No. 4,735,621) is for a tubular condom comprising a flexible, thin-walled tube having at its open end a collar-shaped, outwardly extending portion with a ring-shaped means for radially stretching the collar, which is designed to provide protection against the spread of STD's.

The patent of Wayne (U.S. Pat. No. 2,448,938) describes a sanitary protective appliance which provides a protective cover or hood to cover or protect a body appendage. The appliance has a hood or body portion, with an adhesive layer on an inner face at one open end, and a hollow finger portion at the other end.

Co-pending, commonly-owned application (Ser. No. 07/271,884, now U.S. Pat. No. 4,964,416) for condom articles, discloses a condom and applicator assembly, comprising an applicator ring at the open end of a tubular condom made of a flexible, elastomeric material. In one embodiment of the co-pending application, the ring-shaped applicator has a series of circumferentially spaced apart, longitudinally extending prong elements thereon. The condom applicator assembly comprises the pronged ring having the open end of the condom stretched onto less than all of the prongs when not in use, and stretched over all of the prongs to facilitate penis insertion into the condom.

Packing procedures and devices have been used to maintain sterility and to assist in donning items such as surgical gloves. In the surgical glove package of Poncy et al. (U.S. Pat. No. 4,275,812), the cuff of each surgical glove is contained in a cylindrical ring, which holds the glove open to aid in donning the glove. The cylindrical ring also contains the mouth of a bag that encloses the outer surface of the glove to maintain sterility prior to use. The glove cuff is released from the ring, and the ring and bag removed after the surgeon has put on the gloves.

Because it is important for optimal use of many stretchable devices that must be donned, such as for many types of condom designs, that the open end of the condom not be deformed into a permanently stretched shape during storage, a means of packaging a condom, such as the present invention, that maintains the condom opening in a relaxed position before the package is opened, but provides a means of spreading the opening for donning the condom once the package is opened, simplifies the use of condoms.

It is therefore an object of this invention to provide a means and device for packaging condoms, wherein the packaging serves as a mechanical applicator device to simplify donning a condom.

It is another object of the invention to provide a means and device for packaging many different types and styles of condoms, including those that cannot be rolled up in the usual manner and those that have been lubricated.

Other objects and advantages of the invention will be more fully apparent from the following disclosure and appended claims.

SUMMARY OF THE INVENTION

The present invention in one aspect relates to a package device for a condom in which the package also serves as a mechanical device to aid in donning of the condom. The device comprises an enclosure and one or more attachment means, wherein each attachment means is attached at one end to the enclosure, and attached at a second end to the open end of a condom. For ease in removal of the device from the condom, one end of the attachment means, preferably the end attached to the condom, is releasably attached.

In the first, second and third embodiments of the invention, the enclosure preferably comprises three or more enclosure pieces, one of which has attached thereto one annular ridge or a plurality of hook attachment means, which preferably are molded in one piece with the enclosure. The attachment means may be within the interior of an enclosure piece or located at the edge of an enclosure piece.

In the fourth embodiment of the invention, the enclosure comprises a flat flexible paperform package. The attachment means may comprise a tab glued to the condom at the condom open end, or other means of releasable attachment.

The condom positioned within the package of the various embodiments may be of any structure and formed by any method known in the art, including molding, extrusion, heat sealing or dipping and may comprise an annular ring, flange, or other structure at the condom open end to aid in attaching the condom to the attachment means.

The condom associated with the device of the invention may also comprise adhesives, retention straps (U.S. Pat. No. 4,354,494), elastic garter elements as disclosed in co-pending application Ser. No. 07/271,884, now U.S. Pat. No. 4,964,416 and other devices for attachment of the condom as well as improvements in design and texture.

Other aspects and features of the invention will be more fully apparent from the following disclosure and claims.

DETAILED DESCRIPTION OF THE INVENTION, AND PREFERRED EMBODIMENTS THEREOF

Figure 1:
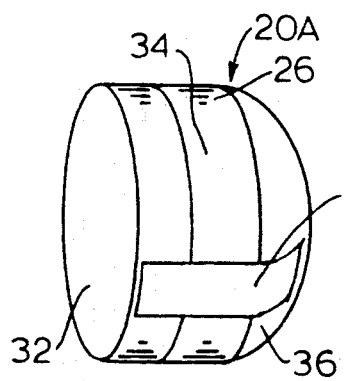
FIG. 1 is a perspective view of the first embodiment of the device of the invention used as a closed package.

In a broad aspect, the device 20(A-D) for packaging and donning a condom, in which the condom 22 has an open condom end 24, comprises:

(a) an enclosure 26 having an interior surface and being convertible from a closed position to an open donning position; and (b) one or more attachment means, each of said attachment means attached to the enclosure 26 and releasably attached to the open condom end 24; wherein said device 20(A-D) functions as a package in the closed position when said enclosure 26 sealingly surrounds said condom 22; wherein said device 20(A-D) functions as a donning device when said enclosure 26 is opened to form separated enclosure pieces, said opening exposing the open condom end 24 for donning; and wherein a user of said condom 22 may remove the device 20(A-D) from the condom 22 by releasing the attachment means.

As discussed herein, the general discussion of the device utilizes the number "20" while the various embodiments are referred to as 20A, 20B, 20C, and 20D.

As used herein, the term "proximal end" refers to the open end 24 of the condom 22 or to the end of the device 20(A-D) of the invention that is closest to the penis when the condom is aligned in the donning device with the opening toward the penis. The term "distal end" herein refers to the closed end 30 of the condom or to the end of the device that is furthest from the penis when the condom is aligned in the device with the opening toward the penis.

The terms "proximally" and "distally" refer to movement toward and away from the body, respectively.

In the first, second and third embodiments of the invention, the enclosure 26 of the device 20A,B,C comprises at least three enclosure pieces: a proximal end cap 32, a donning ring 34, and a distal end cap 36. These enclosure pieces are preferably made of a sturdy material, so that the device 20A,B,C when assembled is not easily deformable.

In these three embodiments, the sturdy material of the three enclosure pieces may comprise a relatively rigid rubber or synthetic plastic substance, a hardened paper or cardboard. The two end caps 32, 36 are preferably a hardened substance, such as a plastic. The donning ring 34 may be of a substance that when formed into a ring is somewhat flexible, such as rubber or a rubbery plastic or is structured so that pressure exerted on the outside of the donning toward the center of the ring and in the plane of the ring causes the ring to deform toward a more oval shape and release the end caps if they are not otherwise sealed to the donning ring 34.

Figure 2:
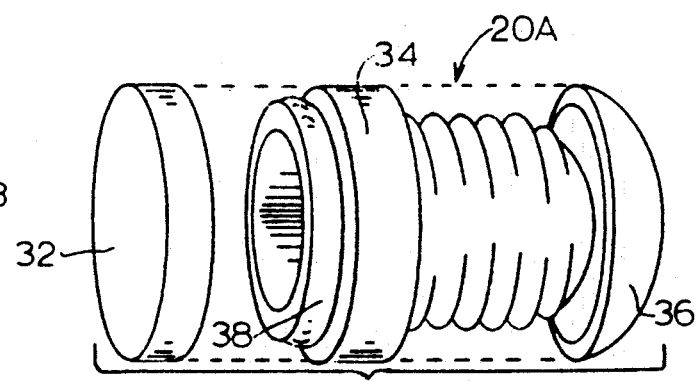
FIG. 2 is a perspective view of the first embodiment of the invention showing the open position.
Figure 3:
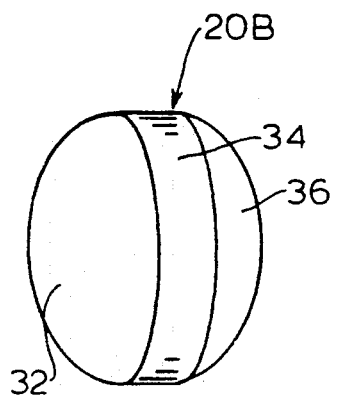
FIG. 3 is a perspective view of the second embodiment of the invention as a closed package.
Figure 4:
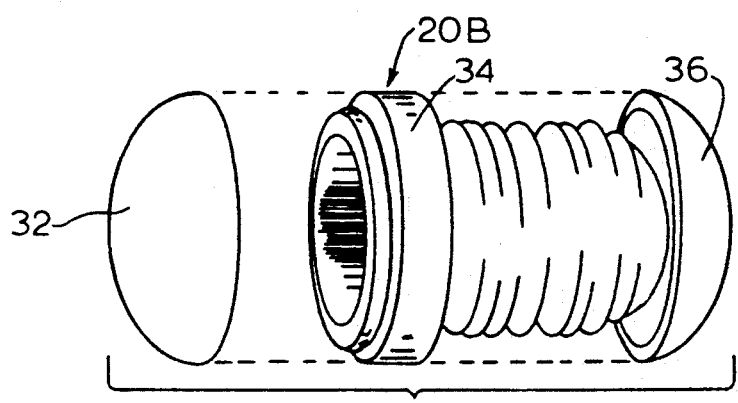
FIG. 4 is a perspective view of the second embodiment of the invention showing the open position.

In the first embodiment of the device 20A of the invention, shown in FIGS. 1-2, the donning ring 34 has a lip protrusion 38 at its proximal end that serves as the attachment means. The condom 22 used with the first embodiment of the invention may have a condom collar or retaining ring 40 at the open proximal end 32 or be undifferentiated from the tubular portion 42 of the condom. Any condom may be used that is attachable over the lip protrusion 38. The condom 22 is held in place by having its open proximal end 24 doubled back over the lip protrusion 38 (FIG. 2). The proximal end cap 32 attaches to the donning ring 34 over the doubled back condom proximal end 24.

The distal end cap 36 in the first embodiment may be either flat or may form a bowed-out distal end to contain the condom 22 in the closed package position.

The condom 20A held in the device of the first embodiment is donned as follows. The proximal and distal end caps 32, 36 are first removed from the donning ring 34. The condom distal end 30 may be allowed to drop free of the donning ring 34 and away from the proximal end 24 of the condom 22. The condom open end 24 is held on the lip protrusion 38 while the donning ring 34 is pulled over the penis to the penis base. The donning ring 34 may then be removed from the condom 22 by pulling the condom open end 24 off the lip protrusion 38, and slipping it distally over the penis and condom distal end 30 before intercourse.

In the second embodiment of the device 20B of the invention, shown in FIGS. 3-6, the donning ring 34 is provided with an attachment means which comprises a hooked annular ridge 44 portion within or at the rim of, the donning ring 34. The hooked ridge 44 has an unhooked portion 46 and a hooked portion 48. Preferably, the unhooked portion 46 of the ridge 44 is firmly attached to the donning ring 34 at either an interior location. or at the exterior rim, of the donning ring 34 of the enclosure as shown in cross-section in FIGS. 5 and 6, respectively. Such attachment to the donning ring 34 may be provided in a permanent manner, such as by molding the donning ring 34 in one piece with the ridge 44 at the interior or rim area of the donning ring 34.

Figure 5:
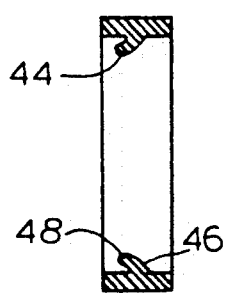
FIG. 5 is a cross-sectional view of the second embodiment of the invention having an interior ridge.
Figure 6:
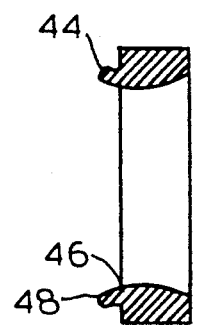
FIG. 6 is a cross-sectional view of the second embodiment of the invention having an exterior ridge.

In the package position of the second embodiment of the device 20B of the invention, the condom open end 24 fits over the hooked portion 48 to hold the condom 22 in place. In FIG. 5, showing an interior location for the hooked ridge 44, the condom open end 24 is held within the donning ring 34. In FIG. 6, showing a rim location for the ridge 44, the condom open end 24 is held at the rim of the donning ring 34.

The hooked annular ridge 44 in the second embodiment may be replaced by a plurality of hooked extensions 50 located around the exterior or interior surface of the donning ring 34 in the same ring area as the hooked ridge 44 is found in the previously discussed variation of the second embodiment. The hooked extensions 50 in this variation of the second embodiment may be structured in a manner similar to that described below for the third embodiment of the invention (FIG. 8).

Figure 7:
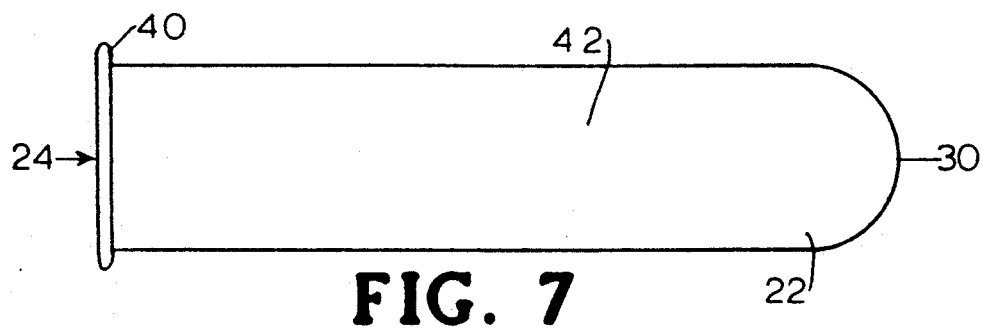
FIG. 7 is a perspective view of a condom with a projecting edge as may be used with the second embodiment of the invention.

The preferred condom 22 used with the second embodiment of the invention comprises a condom with an annular ring 40, ridge or other protruding rim feature at the open end 24 so that it may more easily hook over the hooked portion 48 of the hooked ridge 44 (FIG. 7).

The proximal end cap 32 of the second embodiment may be at least slightly rounded as in the first embodiment or may be flatter in the condoms 22 where the condom open end 24 is held in the interior of the donning ring 34 and does not extend over the rim area of the donning ring 34. The distal end cap 36 in the second embodiment may be the same as in the first embodiment.

Figure 8:
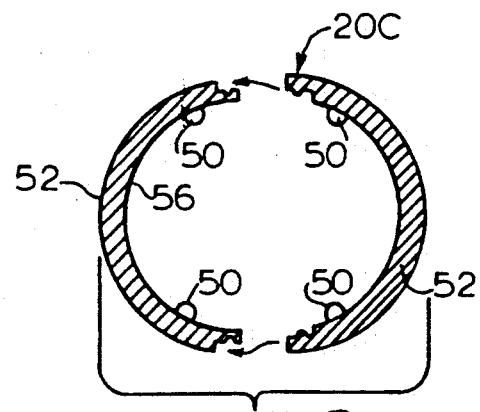
FIG. 8 is a perspective view of the third embodiment of the invention.

The device 20C of the third embodiment of the invention, is similar to that of the second embodiment except that (a) the donning ring 34 is separable transversely into two portions 5 as shown in FIG. 8; and (b) the ridge 44 is replaced by a plurality of hooked extensions 50 in each half of the donning ring 34. Each of the hooked extensions 50 has a releasable hooked first end and is attached to the donning ring 34 at a second end.

The preferred condom 22 for use with the third embodiment invention has an annular retaining ring 40 at its proximal end 24 to assist in positioning the end of the condom 22 over the hooked extensions 50.

In the package position of the third embodiment, the condom open end 24 is preferably held on the hooked ends 54 of the hooked extensions 50 in a relaxed position in which the condom open end 24 is not pulled into an open stretched position. The two portions of the donning ring 34 are held together by seals, a fitted joining area, or by any means known in the relevant art.

When the two portions 52 of the donning ring 34 of the third embodiment are separated after removal of the end caps 32, 36 and prior to donning, the hooked ends 54 on each portion 52 of the donning ring 34 are drawn away from the hooked ends 54 on the other portion 52 of the donning ring 34. The condom rim at the open end 24, which is attached to the hooked extensions 50, is thus stretched open. When there are two hooked extensions 50 on each of portions 52, the condom open end 24 is drawn into a square or rectangular opening. Use of additional hooked extensions 50 results in an opening that more closely approaches a round shape, but increases the number of hooks that must be released from the portions 52 after donning.

The enclosure 26 of the first, second and third embodiments is preferably sealingly closed in the package position, such as by means of an outwardly indented rim area on the proximal end cap 32 that fits within an inwardly indented rim of the donning ring 34. In addition, or in the alternative, one or more seals 58 may be affixed to the outer surfaces of adjacent enclosure pieces to hold them together until the seal(s) 58 are broken prior to use. The enclosure pieces may also be held together by means known in the art.

The distal tubular portion 42 of the condom 22 in the first, second and third embodiments may be folded or positioned in any manner within the donning ring 34 and/or distal cap 36 within the enclosure package 26, with the only requirement being that when the enclosure 26 is properly positioned for opening prior to donning, the tubular portion 42 is below or to the side of the position of attachment of the condom open end 24 to the lip protrusion 38, hooked ridge 44, or hooked extensions 50 or is easily movable to such a position. Thus, when the enclosure 26 is opened, the condom 22 falls easily beneath the rim on the open condom end 24 and does not lie across the top of the condom opening to impede use.

In a fourth embodiment of the device 20D of the invention, the enclosure 26 comprises a flattened flexible package 64 which may be made of paper, foils, or plastics. This package 64 may take a variety of forms such as rectangular, circular, etc.

The package 64 of the fourth embodiment of the packaging and donning device 20D preferably comprises two flat flexible planar members 66 between which the condom 22 is placed (FIGS. 12-15). The planar members 66 are attached to each other at their peripheries around the inserted condom 22 to form a relatively flat package 64. The package 64 may be provided with any type of opening mechanism, such as an edge tear area, a zipper-locked edge area, an openable adhesively sealed edge area.

Figure 10:
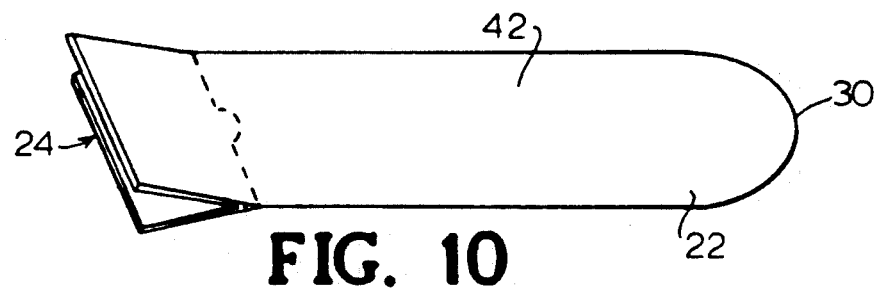
FIG. 10 is a perspective view of a condom with a rectangular flange that may be used with the fourth embodiment of the invention.
Figure 9:
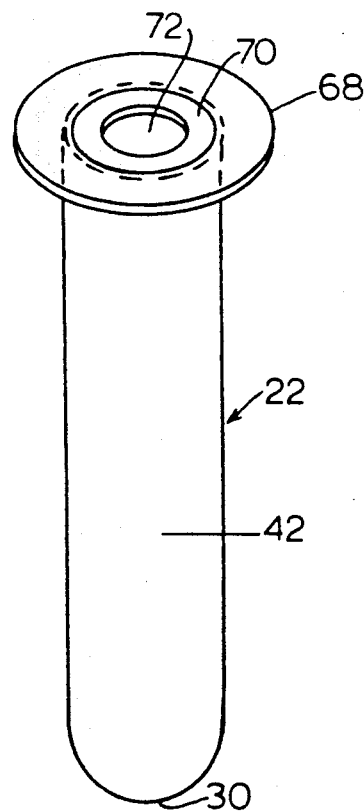
FIG. 9 is a perspective view of a condom with a flange that may be used with the fourth embodiment of the invention.
Figure 11:
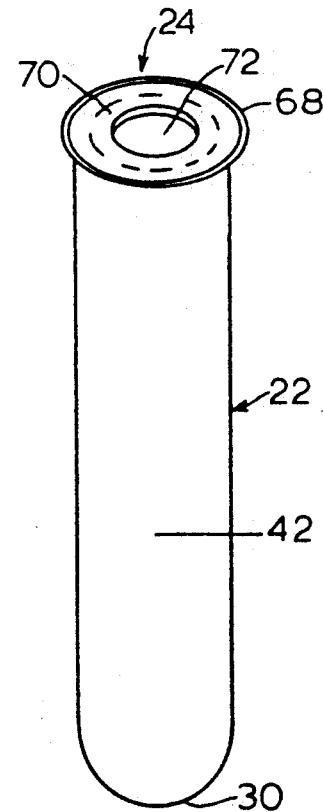
FIG. 11 is another perspective view of a condom with a flange that may be used with the fourth embodiment of the invention.
Figure 12:
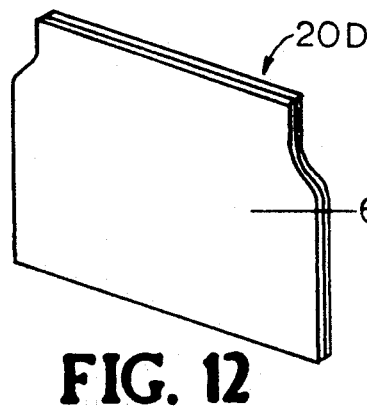
FIG. 12 is a perspective view of the fourth embodiment of the invention as a closed package.

A preferred condom 22 for use with the fourth embodiment of this invention has flaps 67 or a flange 68 at the open end 24 (FIGS. 9-11). Such condoms are disclosed in commonly assigned U.S. patent application, Ser. No. 07/271,884 now U.S. Pat. No. 4,964,416. This condom 22 comprises a main tubular sheath portion 42 which is perimetrally sealed along its edge, and is closed at a distal end 30 and open at a proximal end 24. The extremity of the proximal end 24 is bounded by flaps 67 or a flange 68 which provide extended surface elements for manual gripping to apply the condom 22 to the penis of the wearer. This condom 22 may also have a membrane dam 70 surrounding a central opening 72 as shown in FIGS. 9-11 to prevent fluid flow into or out of the donned condom 22 and to assist in retention of the condom 22 on the wearer's penis.

Figure 13:
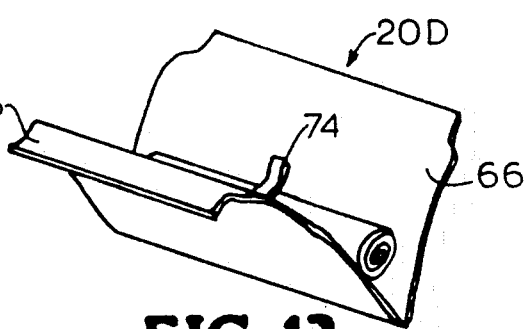
FIG. 13 is a perspective view of the fourth embodiment of the invention partly opened.
Figure 14:
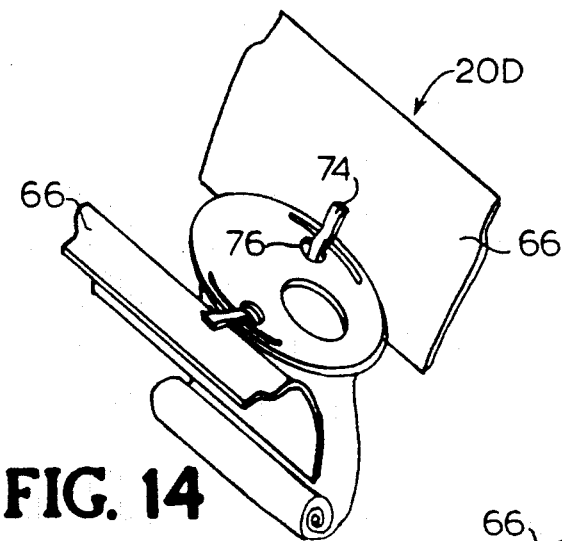
FIG. 14 is a perspective view of the fourth embodiment of the invention completely opened.
Figure 10A:
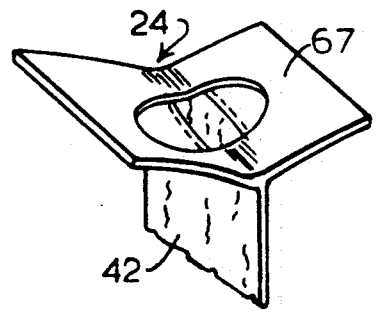
FIG. 10A is a partial perspective view of the condom of FIG. 10 showing the flanges opened.
Figure 15:
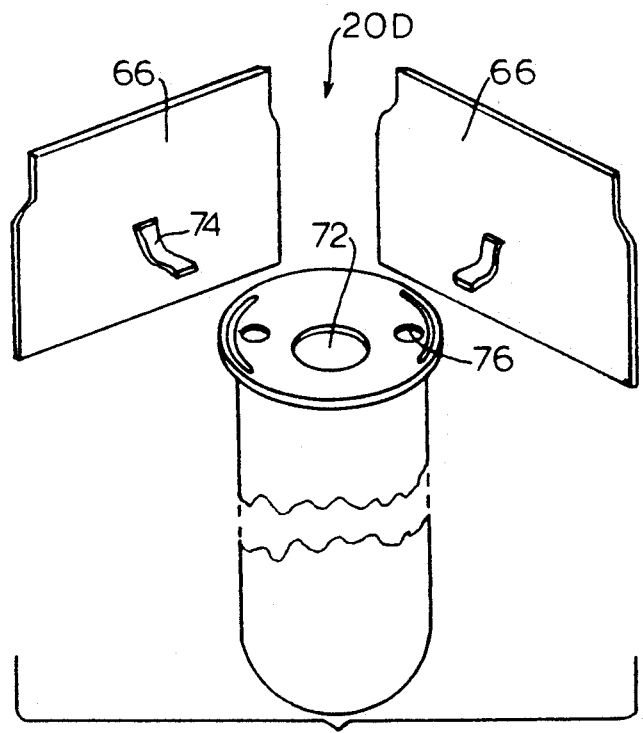
FIG. 15 is a perspective view of the fourth embodiment of the invention with the package removed from the condom.

Each planar member 66 of the device 20D of the fourth embodiment has one or more attachment means extending interiorly from the interior of the planar member (FIGS. 13-15). A double layered planar member 66, with an attachment means formed from a portion of the interior layer and/or extending from the interior layer of each of the two planar members 66 provides package strength and better protects the condom within. Preferably there is at least one attachment means on each planar member. Each attachment means preferably comprises a tab 74 that is releasably attached, such as by an adhesive, to a condom flap 67 or flange 68 on one side of the condom opening 24 opposite from the tab 74 on the other planar member 66. The tab 74 may attach to the upper surface of the flange or flap or may be placed through a hole 76 in the flange or flap (FIGS. 14-15). As an alternative to the tab 74, an adhesive or heat seal may be used to join the condom flange to the package material. The tubular portion 42 of the condom 22 is folded or rolled and located within the package 64 beneath the condom open end 24 when the package 64 is opened.

When the enclosure 26 of the fourth embodiment is opened and the two planar members 66 are moved apart from each other, the open end 24 of the condom 22 is exposed and is positioned with the opening being centrally aligned between the two planar members 66 (FIGS. 13-15). The tubular portion 42 of the condom falls from within the package 64 when the package 64 is opened (FIG. 14). Using the planar members 66 as handles, the donning device and the attached open end of the condom are drawn proximally on the penis and moved rearwardly. The device 20 may then be removed from the condom 22 by either tearing the attachment means, or by twisting the releasably attached glued attachment means from the flange 68 or flap of the condom 22 (FIG. 15).

If the fourth embodiment of the invention is used with condoms 22 which do not contain flanges 68, the tab 74 attachment means may be glued or otherwise attached, preferably in a releasable manner, to the proximal open end 24 of the condom 22, such as to the rim area of the condom or to the side of the proximal end of the condom.

The package 64 of the fourth embodiment may further comprise a series of perforations (not shown) so that the bulk of the package may be separated along the perforations from the attachment means and the area of the package near the attachment means prior to donning.

Other variations in, and combinations of, the embodiments of the invention may be made, including, for example, utilizing tabs as attachment means as in the fourth embodiment, with a hardened three piece enclosure as in the first three embodiments.

Example I

A flanged condom of a selected thermoplastic elastomer material, such as a polyester-based polyurethane or polyurethane elastomer (e.g. ELASTOLLAN TM) is used (FIG. 10). Two roughly rectangular pieces of foil-lined paper (about 2½×2 inches or larger) are prepared with a separate piece of adhesive tape attached at one end to the interior foiled side of each piece of paper. The remaining end of each piece of adhesive tape is attached to one of the flanges of the condom. The tubular end of the condom is rolled up or folded, and placed beneath the condom open end and toward of closer to one of the pieces of paper.

The two pieces of paper are placed together with the condom therebetween and the edges of the two pieces of paper are attached together, such as with an adhesive. Preferably the adhesive along one of the edges (at the top of the condom) is placed in from the edge, to provide an unglued package flap area for gripping and opening the package for use.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. A device for packaging and donning a condom, said condom having an open condom end having flaps or a flange with an upper surface, said device comprising:
   (a) an enclosure having an interior surface and being convertible from a closed position to an open donning position;
   (b) one or more attachment means, each of said attachment means attached to the enclosure and releasably attached to the open condom end, and each of said attachment means extending from said upper surface of said flap or flange to said enclosure;
   wherein said device functions as a package in the closed position when said enclosure sealingly surrounds said condom; wherein said device functions as a donning device when said enclosure is opened to form separated enclosure pieces, said opening exposing the condom open end for donning; and wherein a user of said condom may remove the device from the condom by releasing the attachment means.

2. A device for packaging and donning a condom, said condom having an open condom end, comprising:
   (a) an enclosure having an interior surface and being convertible from a closed position to an open donning position;
   (b) one ore more attachment means, each of said attachment means attached to the enclosure and releasably attached to the open condom end;
   wherein said device functions as a package in the closed position when said enclosure sealingly surrounds said condom; wherein said device functions as a donning device when said enclosure is opened to form separated enclosure pieces comprising a proximal end cap, a donning ring, and a distal end cap; said opening exposing the condom open end for donning; and wherein a user of said condom may remove the device from the condom by releasing the attachment means.

3. A device for packaging and donning a condom according to claim 2, wherein the attachment means comprises a lip protrusion on the donning ring.

4. A device for packaging and donning a condom according to claim 2, wherein the attachment means comprises a hooked annular ridge on the donning ring.

5. A device for packaging and donning a condom according to claim 4, wherein the annular ridge is within the donning ring.

6. A device for packaging and donning a condom according to claim 4, wherein the donning ring has a rim and the annular ridge is at the rim of the donning ring.

7. A device for packaging and donning a condom according to claim 2, wherein the attachment means comprises a plurality of hooked extensions on the donning ring.

8. A device for packaging and donning a condom according to claim 1, wherein the enclosure comprises a flat flexible package formed of two planar enclosure pieces.

9. A device for packaging and donning a condom according to claim 8, wherein the attachment means comprises a tab on the interior of each enclosure piece and each tab is releasably attached to the condom at the condom open end.

10. A device for packaging and donning a condom according to claim 9, wherein the condom open end comprises a flange and the attachment means is releasably attached to the flange.

* * * * *

UNITED STATES PATENT AND TRADEMARK OFFICE
CERTIFICATE OF CORRECTION

PATENT NO.   : 5,170,887
DATED        : December 15, 1992
INVENTOR(S)  : Potts, D. Malcolm et al.

It is certified that error appears in the above-indentified patent and that said Letters Patent is hereby corrected as shown below:

Column 1, line 2, insert the following:

-- GOVERNMENT LICENSE RIGHTS

The invention claimed herein was made under one or more of the following contracts: U.S. Agency for International Development Contract Nos. DPE-3041-A-00-0043 and DPE-0537-A-00-4047, and National Institutes of Health Contract No. N01-HD-2-3143, and the U.S. Government has certain rights therein. --

Signed and Sealed this

Fifteenth Day of April, 1997

Attest:

BRUCE LEHMAN

Attesting Officer           Commissioner of Patents and Trademarks